United States Patent

O'Rourke

Patent Number: 6,010,457
Date of Patent: Jan. 4, 2000

[54] NON-INVASIVE DETERMINATION OF AORTIC FLOW VELOCITY WAVEFORMS

[75] Inventor: Michael Francis O'Rourke, Hunters Hill, Australia

[73] Assignee: PMV Medical Pty Ltd, Ermington, Australia

[21] Appl. No.: 08/913,334

[22] PCT Filed: Mar. 15, 1996

[86] PCT No.: PCT/AU96/00148

§ 371 Date: Sep. 12, 1997

§ 102(e) Date: Sep. 12, 1997

[87] PCT Pub. No.: WO96/29004

PCT Pub. Date: Sep. 26, 1996

[30] Foreign Application Priority Data

Mar. 17, 1996 [AU] Australia .................... PN1798

[51] Int. Cl.⁷ .................................................. A61B 5/00
[52] U.S. Cl. ............................................ 600/500; 600/504
[58] Field of Search ............................ 600/485, 500, 600/503, 504, 505, 526

[56] References Cited

U.S. PATENT DOCUMENTS

| | | | |
|---|---|---|---|
| 4,841,981 | 6/1989 | Tanabe et al. | 600/505 |
| 5,101,828 | 4/1992 | Welkowitz et al. | 600/504 |
| 5,265,011 | 11/1993 | O'Rourke | 600/485 |
| 5,289,823 | 3/1994 | Eckerle . | |
| 5,293,874 | 3/1994 | Takahashi et al. | 600/504 |
| 5,357,967 | 10/1994 | Dixon et al. | 600/526 |
| 5,390,679 | 2/1995 | Martin et al. | 600/526 |
| 5,400,793 | 3/1995 | Wesseling | 600/504 |

FOREIGN PATENT DOCUMENTS

| | | |
|---|---|---|
| 0 487 726 A1 | 6/1992 | European Pat. Off. . |
| WO 88/01773 | 3/1988 | WIPO . |

OTHER PUBLICATIONS

"Peripheral Pulse Contour Analysis in Determining Stroke Volume" by H.A.J. Lasance, K.H. Wesseling, C.A. Ascoop. Chapter 10: "Effect of the Splanchnic Circulation on the Formation of the Arterial Pulse", by Mustafa Karamanoglu, Stimulation, Measurement and Analysis of the Propagating Pressure Pulse in the Human Arterial System, University of New South Wales, Dec., 1992, pp. 196, 209–214.

Primary Examiner—Robert L. Nasser
Attorney, Agent, or Firm—Baker & Daniels

[57] ABSTRACT

A method is disclosed for determining the aortic flow velocity waveform non-invasively. A calibrated ascending aorta pressure waveform can be derived from peripheral measurements, for example at the radial artery, and calibrated from conventional syphgmomanometry, for example at the brachial artery. From the calibrated ascending aorta pressure waveform the flow velocity waveform in the ascending aorta can be determined, by using the Fourier transform of the pressure waveform and the age-related phase and modulus values. The method can also be used for invasively measured pressure waveforms to provide a flow waveform.

22 Claims, 3 Drawing Sheets

NON-INVASIVE DETERMINATION OF AORTIC FLOW VELOCITY WAVEFORMS

TECHNICAL FIELD

The present invention relates to the derivation of aortic flow waveforms, using non-invasive techniques, in particular, measurement of pressure waveforms in peripheral arteries.

BACKGROUND ART

It is desirable in a wide range of clinical applications to be able to assess the flow velocity waveform in the ascending aorta. Flow velocity may be defined as average volume per second per unit area of the vessel. Flow velocity may be converted to actual volume per second if the vessel's internal diameter is known or determined. For the purposes of this determination, the velocity profile across the vessel may be assumed to be flat—we are here concerned with overall volume flow and rate of flow.

Flow velocity data is useful, for example, in assessing patients presenting with symptoms of cardiac disease, hypertension, and angina pectoris, and in following the response of these patients to treatment. However, techniques in use for assessing these parameters have not been appropriate for routine use. One known invasive technique utilises a probe inserted into an artery. It is also possible to utilise ultrasonic echo flow techniques, however, this has the drawback of using relatively expensive and complex equipment, and requiring a very high level of skill on the part of the operator to produce reliable results.

In a paper, "Computation of aortic flow from pressure in humans using a non-linear, three element model", J. Appl. Physiol. 74(5):2566–2573, 1993, Wesseling et al disclose a method for computing aortic flow from radial pressure waveforms. The calculations described use a Windkessel type model, and whilst some account is taken of age, no account is taken of wave reflection, the timing of wave reflection, nor the changes in wave reflection or impedance which occur with age.

In a paper by Fry DL, "The measurement of pulsatile blood flow by the pressure gradient technique", IREE Transactions on Medical Electronics 6:259–264, 1959, an analog processing arrangement was used to produce a derived flow wave, with criteria imposed relating to the observed characteristics of the system. In particular, the flow wave at the incisura (identified by a flag) was required to approach zero, or pass from positive to negative within 10 ms of the incisura, and flow during diastole is required to be zero or within 3% of zero compared to peak systolic flow, and to show no systematic increase or decrease during diastole.

SUMMARY OF INVENTION

According to a first aspect the present invention provides a method for determining an aortic flow velocity waveform, comprising the steps of:

a. measuring non-invasively at a peripheral site a blood pressure pulse waveform;

b. calibrating the blood pressure pulse waveform by reference to systolic and diastolic pressures measured at a site comparable to the peripheral site, and thereby calibrating the waveform of (a);

c. calculating the calibrated aortic pressure pulse waveform at the ascending aorta using said calibrated blood pressure pulse waveform and a predetermined transfer function;

d. calculating the aortic flow velocity waveform from said aortic pressure pulse waveform by reference to predetermined values for age dependant impedance modulus and phase difference between the aortic pressure pulse waveform and the aortic flow velocity waveform.

Preferably, a further step e is performed, in which the calculated flow velocity waveform is examined to determine whether the waveform meets predefined criteria, and if it does not, then the assumed age value is varied in a process of iteration until the waveform does meet said criteria.

Preferably, said predefined criteria include requirements that at the time of incisura, (that is, during diastole) the flow is substantially zero, and that after incisura flow remains beneath a predetermined percentage, say 3%, of peak flow relative to zero.

The latter requirement seeks to ensure that computed values correspond to the reality that after incisura, the aortic valve is shut and there is no driving pressure, and accordingly apart from minor effects no positive or negative flow will occur.

Step d is preferably performed by performing Fourier analysis on the derived pressure waveform, calculating the flow wave components corresponding to each frequency component of the pressure wave separately, and combining the resulting waveforms to provide a derived flow velocity waveform.

It will be understood that the present invention may be applied to produce an uncalibrated waveform, which may be of use in some situations, although the calibrated version is preferred.

According to a second aspect the present invention provides a method for determining an aortic flow velocity waveform from a measured or derived ascending aortic pressure pulse waveform, comprising the steps of:

calculating the aortic flow velocity waveform from said aortic pressure pulse waveform by reference to predetermined values for age dependant modulus, and phase difference between flow and pressure waves, at various frequencies.

Preferably, a further step is performed, in which the calculated flow velocity waveform is examined to determine whether the waveform meets predefined criteria, and if it does not, then the assumed age value is varied in a process of iteration until the waveform does meet said criteria.

Preferably, said predefined criteria include requirements that at the time of incisura, (that is, during diastole) the flow is substantially zero, and that after incisura flow remains within a predetermined margin, say 3%, of peak flow relative to zero.

It is preferred that the flow waveform is derived by performing Fourier analysis on the derived pressure waveform, calculating the flow wave components corresponding to each frequency component of the pressure wave separately, and combining the resulting waveforms to provide a derived flow velocity waveform.

The values for modulus and phase are preferably as described hereinafter, however, it will be appreciated that such values may alternatively be determined by conducting appropriate further clinical studies.

The present invention provides a relatively simple, non-invasive procedure for determining calibrated velocity flow waveforms in humans, which takes account of variations of impedance and phase with age. Moreover, by performing an iteration of age to ensure the output derived waveform matches real parameters, a separate indication of the apparent "age" of the vascular system of the patient can be provided, which may in itself be of clinical relevance.

BRIEF DESCRIPTION OF DRAWINGS

An embodiment of the present invention will now be described with reference to the accompanying figures, in which.

DESCRIPTION

The present invention relies on the use of an ascending aortic pressure waveform derived from a peripheral pressure waveform, and so initially this process will be briefly described. This procedure is discussed in more detail in U.S. Pat. No. 5,265,011 to O'Rourke, in a paper, "An analysis of the relationship between central aortic and peripheral upper limb pressure waves in Man", Karamanoglu, O'Rourke, Avolio and Kelly, European Heart Journal (1993) 14, 160–167, and in the texts "The Arterial Pulse", O'Rourke, Kelly and Avolio, published by Lea Febiger, Philadelphia 1992 and "Arterial Vasodilation", O'Rourke, Saffer, Dzau, published by Arnold, London 1993. Reference should be made to these documents if clarification is required of this part of the process.

Figure 3:
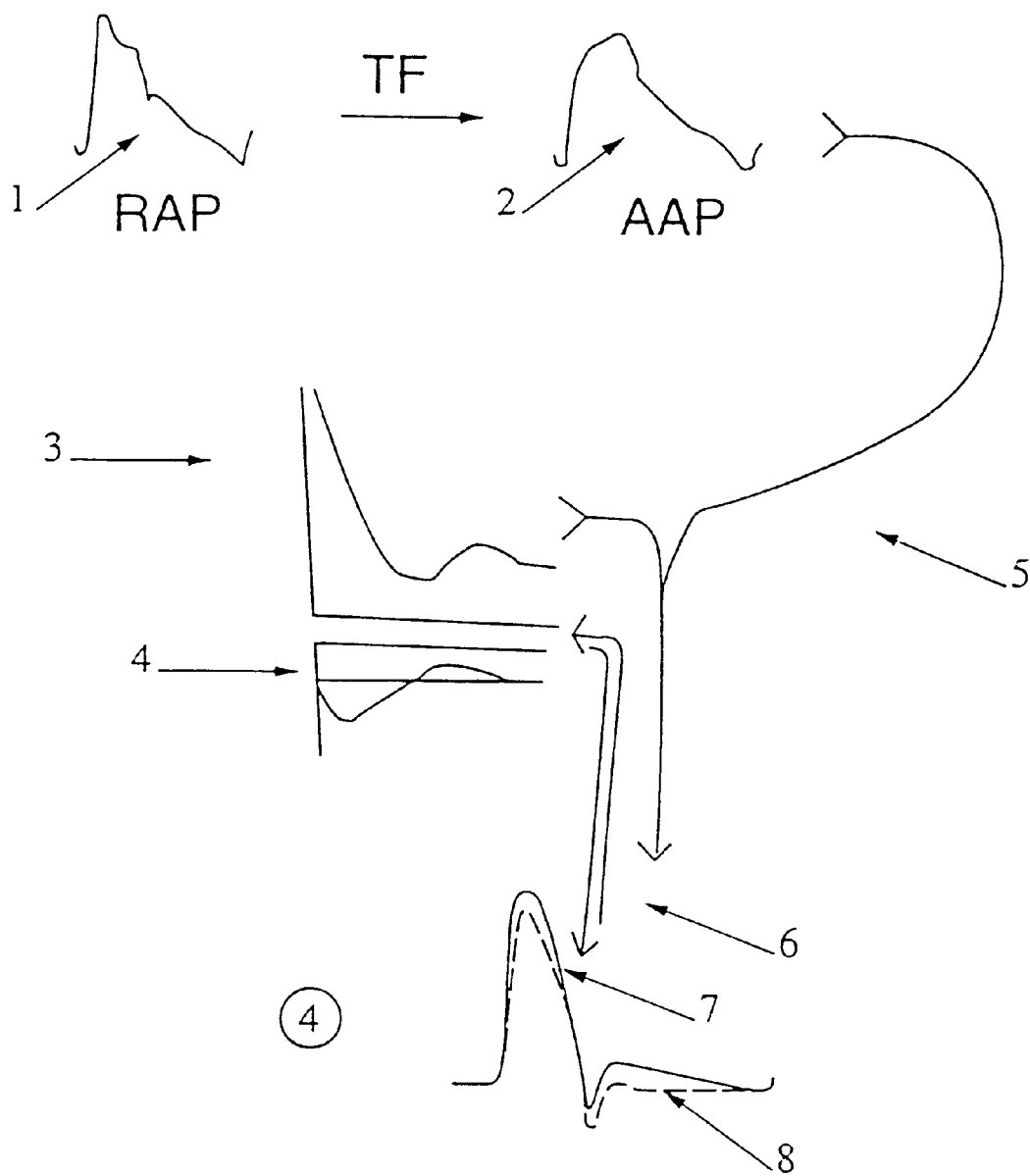
FIG. 3 illustrates graphically the calculation process for the derived flow velocity waveform according to a preferred calculation technique.

Briefly, the pressure waveforms of the peripheral arteries can be related to the ascending aortic waveform, by means of a clinically determined transfer function. This transfer function is most readily applied by deriving the Fourier transform of the measured waveform, applying the transfer function to each component sinusoid, and combining the calculated values. The measured waveform may be calibrated by measuring the systolic and diastolic pressures, using conventional sphygmomanometry, at a site comparable to the waveform measurement site. For example, it is convenient to measure waveforms at the radial artery, and to calibrate this from the brachial artery. FIG. 3 shows a sample waveform 2 for the ascending aortic pressure, labelled as AAP. This has been derived from the radial waveform RAP, using transfer function TF. It will be appreciated, however, that the present invention is not limited in scope to utilising the exact procedures and transfer functions of the O'Rourke patent to derive the AAP waveform.

The above cited O'Rourke patent further describes a technique for the automatic determination of the point of incisura, using the third derivative of the measured peripheral pulse, by locating a zero crossing from positive to negative in proximity to the largest maximum point of the third derivative after the peak of a second systolic shoulder. However, it is contemplated that an implementation may allow for the point of incisura to be manually overridden by the physician based upon his interpretation of the waveform. An alternative method for calculating or otherwise determining the point of incisura may be utilised within the present invention if desired. The point of incisura is particularly relevant to the preferred implementation, as will be described below.

It will be understood that the calculation and processing described below may be readily implemented in a microprocessor type device using well understood software techniques, most conveniently in a laptop or other portable computer. Any suitable calculating and processing device may be used to implement the inventive techniques.

Figure 1:
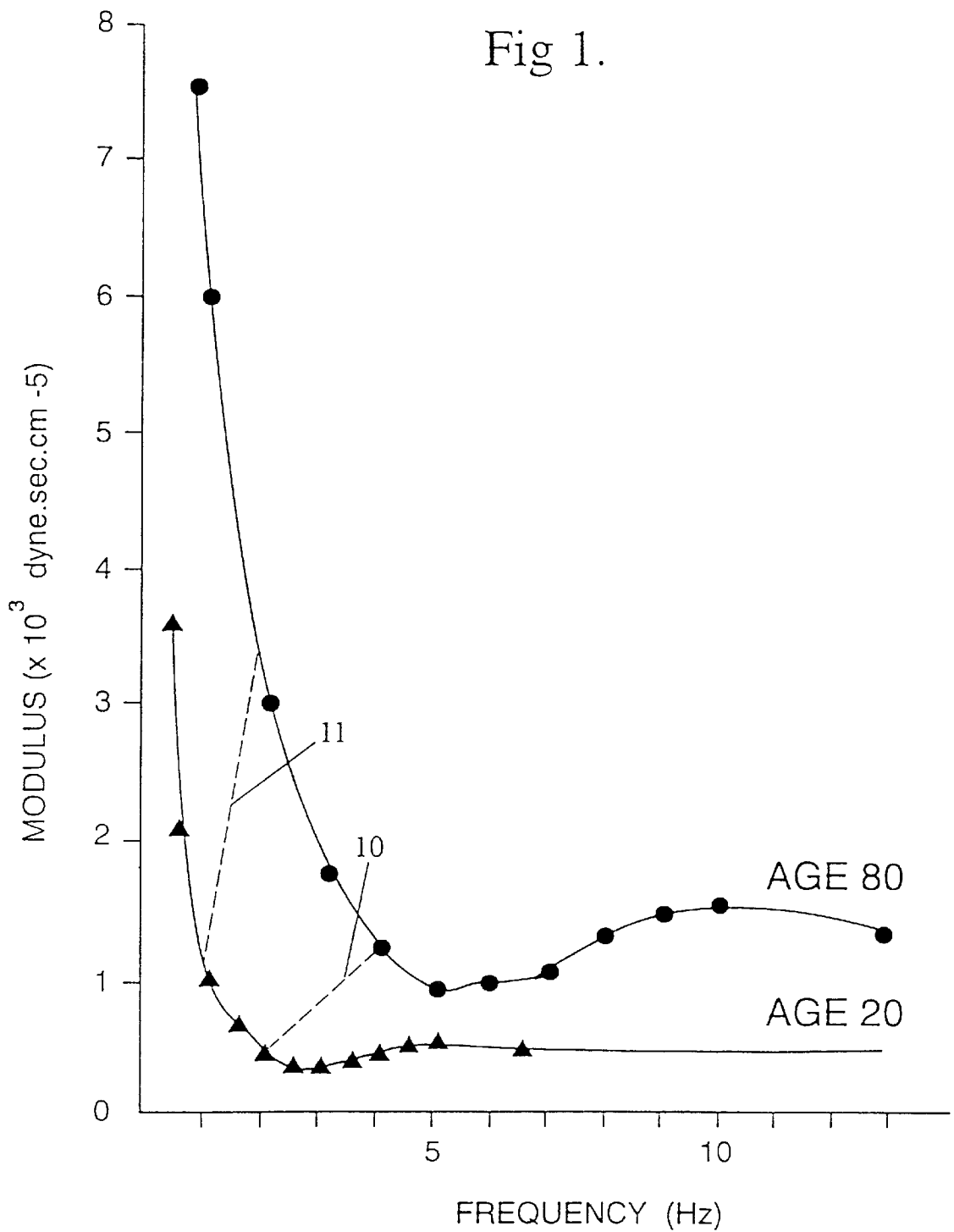
FIG. 1 illustrates ascending aortic impedance modulus as a function of frequency for ages 20 and 80.

FIG. 1 shows a plot of modulus against frequency, for ages 20 and 80. "Modulus" is a known term of art, and is a measure of the bulk elasticity of the circulatory system. Although if desired a more elaborate set of interpolations could be used to implement the present invention, a reasonable value of modulus for intervening ages can be determined by an interpolation procedure as will be described below. Fully grown subjects under 20 may be assumed to be 20; over 80 may be assumed to be 80. The modulus may be considered as a linear impedance value, which can be applied at the frequency of each frequency component of the Fourier series of the derived aortic pressure pulse. The amplitude of each frequency component is determined by dividing by the respective modulus value. In other words, the amplitude of each of the frequency components of the previously described Fourier series is to be divided by the respective modulus values in order to find the amplitudes of the frequency components of the transformed signal.

Considering the curves in FIG. 1, it has been determined clinically that the general trend of the curves with age is that an equivalent point for any given frequency on the age 20 curve corresponds to a point at twice that frequency on the age 80 curve, and this relationship can be used to provide a basis for interpolation.

Hence, interpolation may be performed by taking points at, for example, 0.5 Hz intervals on the age 20 curve, taking points on the age 80 curve at twice the frequency of the corresponding age 20 points, and drawing a line between the curves. Ilustrative interpolation lines are shown on FIG. 1 as lines 10 and 11. Along each line, a point can be marked at a fraction of the distance along the line from the age 20 curve corresponding to the modulus curve at a given intervening age X using the relation:

$$F_x = (X-20)/60$$

to give the fraction $F_x$ required along each line. For example, for a 35 year old, the fraction along each line is 0.25 along each line measured from the age 20 point.

It will be appreciated that if further clinical data is available for intervening ages, then a similar process could be used between each curve for which data was available. It is preferred that this aspect be implemented as a look-up table in a device. It will be understood that it is only the modulus value of each age curve which is required at discrete frequency component values, not the entire curve. Hence, it will be appreciated that an entire set of curves could be readily calculated and the values at suitable intervals stored in a look up table for use during automatic calculation.

Figure 2:
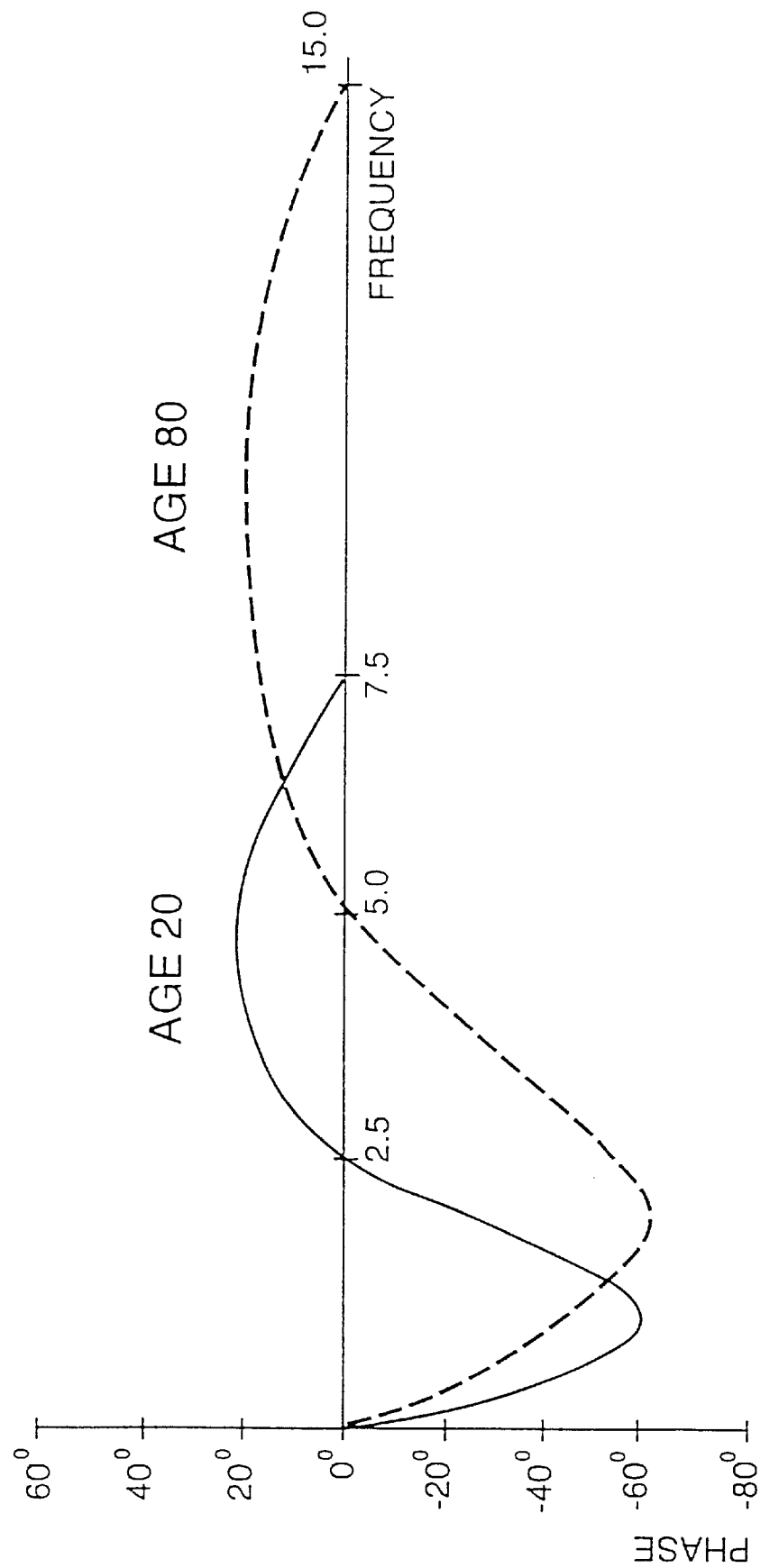
FIG. 2 illustrates ascending aortic impedance phase, as a function of frequency, for ages 20 and 80.

FIG. 2 illustrates the phase difference between the pressure and flow waves in the ascending aorta, at different frequencies, once again for ages 20 and 80. It will be appreciated that as a person ages, compliance is reduced, and so the pattern of flow propagation resulting from a given pressure stimulus is different. Again, for ages between 20 and 80, a linear interpolation can be performed to derive the corresponding phase diagrams for intermediate ages. Again, it is preferred that the values be stored for suitable frequency and age values in a look up table.

FIG. 3 illustrates the calculation process graphically. The calibrated ascending aortic pulse waveform AAP 2 is derived from the calibrated radial artery waveform 1, as previously described. The resulting waveform is then subjected to Fourier analysis. The lower frequency component is, in general, dominant, and useful results can be derived by utilising only a limited number, for example the first 8 to 10 frequency components (i.e., the fundamental frequency and first 7, 8 or 9 harmonics). Of course, if more frequency components are used, the overall accuracy will be improved, particularly if it is desired to characterise the short negative flow period typically occurring after the incisura.

For each frequency component, the age related modulus value for the sinusoid's frequency from FIG. 1, referenced here as 3, is used to determine the amplitude of the corresponding flow wave component, and the phase difference from FIG. 2, here referenced as 4, is used to define the phase of the corresponding component. At this stage, an input value for age, being either the patient's actual age or the physician's estimated alternative value, is used. The resulting waveforms are combined, to produce an output flow waveform 7.

In a preferred implementation, this waveform is then tested against criteria which any flow waveform of this type must possess. One such characteristic is that after incisura, the time of which is known from the RAP to AAP process, the flow waveform must be zero. A second is that after incisura, the waveform must remain within a defined margin, for example 3%, of peak flow. Other criteria could be used in addition if desired. This could be performed manually, or within the processor of the present invention.

If the resulting waveform does not meet these criteria, or correspond within defined. limits, then a process of iteration is commenced, in which the "age" value is varied up and down, and the flow waveform recalculated, until a best fit waveform 8 is determined. Ideally, this imputed age is available by display or otherwise to the physician. Although not necessarily determinative of any condition, the necessity to impute an age of, say, 60 to obtain a best fit for a man whose chronological age is 45 may be of clinical relevance.

Much of the process of calculation required to be implemented according to a preferred implementation in software differs only in detail from the existing software used to implement the derivation of pressure waveforms at the ascending aorta from the radial waveform, and so no detail will be provided. From the calculation of the ascending aorta waveform, the Fourier series of this waveform in already known. For each frequency component, a lookup table is used to provide the phase and modulus values for the age or imputed age of the patient, and the fourier transform of the flow waveform is derived. If the predefined criteria mentioned above are not met, the process is repeated using successive age values until the best fit is found. This type of software process is well understood by those skilled in the art.

It will be appreciated that while the present invention is directly concerned with determining the flow waveform, as this is a calibrated measurement it can be used to calculate the volume rate of flow. A value for the diameter, and hence area, of the aorta may be obtained from standard tables or formulae, or may have been obtained clinically, for example from echocardiography.

It will be appreciated that more elaborate impedance modulus and phase values, including other factors such as sex, or more detailed intermediate measurements, could be utilised. Additionally, further factors may be used in the transfer functions to derive the AAP waveforms, for example age, height and blood pressure. In comparison to their influence on impedance, these effects on transfer function for pressure are small It will be appreciated that variations and additions are possible within the spirit and scope of the invention.

I claim:

1. A method for determining an aortic flow velocity waveform, including the steps of:

a. measuring non-invasively at a peripheral site a blood pressure pulse waveform;

b. calibrating said blood pressure pulse waveform by reference to systolic and diastolic pressures measured at a site comparable to said peripheral site; and c. calculating the calibrated aortic pressure pulse waveform at the ascending aorta using said calibrated blood pressure pulse waveform and a predetermined transfer function;

d. calculating the aortic flow velocity waveform from said aortic pressure pulse waveform by reference to predetermined values for age dependent impedance modulus and phase difference between said aortic pressure pulse waveform and said aortic flow velocity waveform.

2. A method according to claim 1, including the further step of:

(e) determining whether the waveform calculated at (d) meets predefined criteria, and if it does not, then repeating step (d) iteratively using different values for age until said waveform meets said predefined criteria.

3. A method according to claim 2, wherein said method includes storing an input or calculated time value for the point of incisura for said calibrated aortic pressure pulse waveform, and said predefined criteria include that at the point of incisura, the flow is substantially zero.

4. A method according to claim 3, wherein said predefined criteria include that after incisura flow remains beneath a predetermined percentage of peak flow.

5. A method according to claim 2, and including outputting a value for the imputed age at which said predefined criteria are met.

6. A method according to claim 1, including performing step (d) by using the Fourier transform of said calibrated aortic pressure pulse waveform, calculating the flow wave components corresponding to each frequency component of the pressure wave separately, and combining the resulting waveforms to provide a derived flow velocity waveform.

7. A method according to claim 6, including in step (d) determining the flow wave component for each frequency component of the Fourier transform by reference to values for modulus and phase for each frequency within predefined age bands stored in a look up table.

8. A method for determining an aortic flow velocity waveform from a measured or derived ascending aortic pressure pulse waveform, comprising calculating the aortic flow velocity waveform from said aortic pressure pulse waveform by reference to predetermined values for age dependent impedance modulus and phase difference between said aortic pressure pulse waveform and said aortic flow velocity waveform.

9. A method according to claim 8, including the further step of determining whether the flow waveform meets predefined criteria, and if it does not, then repeating said calculation step iteratively using different values for age until said waveform meets said predefined criteria.

10. A method according to claim 9, wherein said method includes storing an input or calculated time value for the point of incisura for said ascending aortic pressure pulse waveform, and said predefined criteria include that at the point of incisura, the flow is substantially zero.

11. A method according to claim 9, and outputting a value for the imputed age at which said predefined criteria are met.

12. A method according to claim 8, including performing said calculating step by using the Fourier transform of said ascending aortic pressure pulse waveform, calculating the flow wave components corresponding to each frequency component of the pressure wave separately, and combining the resulting waveforms to provide a derived flow velocity waveform.

13. A method according to claim 8, wherein said calculating step is performed using the Fourier transform of said ascending aortic pressure pulse waveform, calculating the flow wave components corresponding to each frequency component of the pressure wave separately, and combining the resulting waveforms to provide a derived flow velocity waveform.

14. A method according to claim 13, and including in said calculating step, determining the flow wave component for each frequency component of the Fourier transform by reference to values for modulus and phase for each frequency within predefined age bands stored in a look up table.

15. A method for representing an aortic flow velocity waveform by calculating parameters defining an aortic flow velocity waveform as a function of:

parameters defining an ascending aortic pressure pulse waveform and predetermined values for age dependent impedance modulus and phase difference between said aortic pressure pulse wavefom and said aortic flow velocity waveform;

and plotting an aortic flow velocity waveform defined by said aortic flow velocity waveform parameters.

16. A method according to claim 15 wherein said calculated parameters are examined to determine if they meet predefined criteria before plotting, and if determined not determined to meet said criteria then said calculation is repeated iteratively using different values for age until said calculated parameters do meet said predefined criteria.

17. A method according to claim 16 wherein said method includes storing an input or calculated time value for the point of incisura for said ascending aortic pressure pulse waveform, and said predefined criteria include that at the point of incisura, the flow is substantially zero.

18. A method according to claim 17, wherein said predefined criteria include that the after incisura flow remains beneath a predetermined percentage of peak flow.

19. A method according to claim 18, including performing said calculating step by using the Fourier transform of said ascending aortic pressure pulse waveform, calculating the flow wave components corresponding to each frequency component of the pressure wave separately, and combining the resulting waveforms to provide a derived flow velocity waveform.

20. A method according to claim 19, and in said calculating step, determining the flow wave component for each frequency component of the Fourier transform by reference to values for modulus and phase for each frequency within predefined age bands stored in a look up table.

21. A method according to claim 20, and outputting a value for the imputed age at which said predefine criteria are met.

22. A method according to claim 15 and causing said representation to appear on a computer monitor.

* * * * *

UNITED STATES PATENT AND TRADEMARK OFFICE
CERTIFICATE OF CORRECTION

PATENT NO. : 6,010,457
DATED : January 4, 2000
INVENTOR(S) : Michael Francis O'Rourke It is certified that error appears in the above-identified patent and that said Letters Patent is hereby corrected as shown below:

ON THE TITLE PAGE:

Item [73]

Assignee: delete "PMV" and substitute therefor --PWV--

Signed and Sealed this

Twenty-third Day of January, 2001

Attest:

Attesting Officer

Q. TODD DICKINSON
Commissioner of Patents and Trademarks